(12) United States Patent
Sauar et al.

(10) Patent No.: US 7,920,738 B2
(45) Date of Patent: Apr. 5, 2011

(54) ESTABLISHING CORRESPONDENCE AND TRACEABILITY BETWEEN WAFERS AND SOLAR CELLS

(75) Inventors: Erik Sauar, Oslo (NO); Tor Christian Tuv, Rasta (NO)

(73) Assignee: Renewable Energy Corporation ASA, Hovik (NO)

( * ) Notice: Subject to any disclaimer, the term of this patent is extended or adjusted under 35 U.S.C. 154(b) by 969 days.

(21) Appl. No.: 10/598,123

(22) PCT Filed: Feb. 18, 2005

(86) PCT No.: PCT/NO2005/000061
§ 371 (c)(1),
(2), (4) Date: Oct. 6, 2006

(87) PCT Pub. No.: WO2005/080950
PCT Pub. Date: Sep. 1, 2005

(65) Prior Publication Data
US 2008/0160648 A1    Jul. 3, 2008

(30) Foreign Application Priority Data
Feb. 20, 2004   (NO) .................................. 20040756

(51) Int. Cl.
*G06K 9/00* (2006.01)
*H02N 6/00* (2006.01)
(52) U.S. Cl. ................... 382/145; 382/141; 136/249
(58) Field of Classification Search ............ 382/145, 382/141; 356/72, 237.1, 30, 394, 237.5; 438/8, 4, 16, 800, 199, 67, 74; 257/E21.525, 257/E23.17, E21.41, E27.12, 432, 440, E25; 136/249, 246, 243; 250/206.1, 208.6, 492.2; 365/201, 226, 78, 174, 220; 326/41, 39, 47; 430/318; 716/4, 8
See application file for complete search history.

(56) References Cited

U.S. PATENT DOCUMENTS
4,256,681 A * 3/1981 Lindmayer .................. 264/85
(Continued)

FOREIGN PATENT DOCUMENTS
JP          6-77509          3/1994
(Continued)

OTHER PUBLICATIONS

"Automation and Control Solution", Cimarron Computer Engineering Inc., http://web.archive.org/web/20040211113118/cceinm.com/automation.html Published latest Jan. 23, 2004.
(Continued)

*Primary Examiner* — Sheela C Chawan
(74) *Attorney, Agent, or Firm* — Christian D. Abel

(57) ABSTRACT

The invention regards a method and a system for establishing correspondence between wafers and solar cells produced from said wafers. The method comprises for each wafer and each solar cell, providing an image of the wafer, providing an image of the cell, comparing the wafer image to the cell image, upon match between a cell image and a wafer image, assigning the current cell to the current wafer. The system comprises at least one imaging device for providing images of the wafers and the cells, a processing unit for comparing a wafer image to a cell image, and upon match between a cell image and a wafer image, assigning the current cell to the current wafer, and a memory unit.

19 Claims, 5 Drawing Sheets

U.S. PATENT DOCUMENTS

| | | | | |
|---|---|---|---|---|
| 5,716,459 | A | * | 2/1998 | Chang et al. .................. 136/249 |
| 5,757,474 | A | * | 5/1998 | Sopori et al. .................... 356/72 |
| 6,140,140 | A | * | 10/2000 | Hopper ............................. 438/8 |
| 6,482,661 | B1 | * | 11/2002 | Madoyski ....................... 438/14 |
| 7,065,239 | B2 | * | 6/2006 | Maayah et al. ............... 382/145 |
| 7,144,457 | B1 | * | 12/2006 | McRee et al. .................... 117/2 |

FOREIGN PATENT DOCUMENTS

| | | |
|---|---|---|
| JP | 07022635 | 1/1995 |
| JP | 08046229 | 2/1996 |
| JP | 9-129578 | 5/1997 |
| JP | 10321690 | 4/1998 |
| JP | 10-256106 | 9/1998 |
| JP | 2001-313274 | 9/2001 |
| JP | 2003-243675 | 8/2003 |
| WO | WO 02/077621 | 10/2002 |

OTHER PUBLICATIONS

Office Action dated Aug. 31, 2010 from Japanese Patent Office.

* cited by examiner

ESTABLISHING CORRESPONDENCE AND TRACEABILITY BETWEEN WAFERS AND SOLAR CELLS

FIELD OF THE INVENTION

The present invention is related to production of solar cells, and more precisely to a method and a system for establishing correspondence between wafers and solar cells produced from said wafers, to provide solar cell traceability.

BACKGROUND OF THE INVENTION

A solar cell panel comprises a matrix of solar cells, which convert sun light into electricity. Each solar cell is produced by treating a silicon wafer. Silicon wafers are cut out of a large silicon body called ingot.

The ingot is manufactured in a furnace, and good care is taken to control among other things the ingot's temperature during manufacturing, since it plays a very important role in defining the quality of the ingot.

A large ingot has normally an uneven quality. This uneven quality is reflected in the wafers cut from the ingot and in the cells, and it will lie as a bottom line governing the wafer and cell characteristics.

Cell quality can be measured swiftly and reliably. Usually cell quality is determined by means of an inspection, where the cell's surface, current, voltage, efficiency and shunt resistance are measured. Ingot and wafer quality can not be measured as precisely as cell quality, and a full characterization of wafer and ingot quality always includes cell processing of the materials. Detailed wafer and ingot quality measurements are very costly and require several weeks of testing, which makes them unsuitable for a production process.

The invention has thus as an object to provide a method for establishing correspondence between a cell and a wafer, that is, identifying which cell is produced from which wafer.

By means of the invention cell quality will easily be correlated to wafer and ingot quality and the furnace and other production parameters can be modified to increase the electrical quality and mechanical strength of both wafers and cells.

There are several methods for tracing a cell back to a wafer:
1) Wafer scribing/inking: An identification of the wafer is written on the wafer's surface by means of a marker, as described in e.g. U.S. Pat. No. 6,482,661. A plurality of wafers are sliced from the ingot with a portion of the ingot indicia. Wafer indicia is then marked on the peripheral edge of the wafer. Said indicia is read by means of a camera and information is stored. JP 10321690 describes a method where a wafer number is printed in the peripheral part of a surface where a pattern is not formed. The wafer number is read by means of a CCD camera and recognized by a recognizing part. These methods have the disadvantage that they lead to reduction in the wafer's surface quality. They are besides not suitable for mass production.
2) A small cut is performed on the wafer. This method leads to increased breakage ratio.
3) Tracking by means of advanced data systems (e.g. as described in U.S. Pat. No. 6,330,971) which "follow" a wafer during all the process. This alternative is highly expensive as it requires adapting the tracking system to equipment produced by different entities.

Alternatives 1) and 2) are presently only used in the field of research. Alternative 3) is possibly used for very high amounts of cells, where the size of the batches justifies a high investment in tracking system, but to the applicant's knowledge this is not used in mass production today.

SUMMARY OF THE INVENTION

The present invention has as an aim to provide a method and a system which do not modify the wafer's surface, and at the same time do not require adapting the tracking system to different pieces of equipment.

This object is achieved by means of a method and a system for establishing correspondence between wafers and solar cells produced from said wafers. Said method comprises, for each wafer and each solar cell, a) providing an image of the wafer,
b) providing an image of the cell,
c) comparing the wafer image to the cell image,
d) upon match between a cell image and a wafer image, assigning the current cell to the current wafer.

The invention is based on the concept that the crystallographic structure is unique for each wafer, and that this structure is visible both in the wafer and in the manufactured cell, so that crystallographic image information is sufficient to establish a correspondence between a cell and a wafer.

According to one aspect of the invention, the steps a) and b) in the above mentioned method comprise depicting the crystallographic structure of the wafer and the cell, while step c) comprises comparing said crystallographic structures to one another.

No identification is applied to the wafer surface, since the wafer's and the cell's own appearance due to their crystallographic properties are used for identification.

Once a correspondence is established, it can e.g. be used to assign wafer data to each cell. According to one aspect of the method disclosed, it comprises linking wafer identification data to the corresponding cell.

If breakage of a wafer occurs during cell manufacturing, that particular wafer will be removed from the production line and there will not be a cell image matching the wafer image of that wafer. If no cell image match a particular wafer image, this wafer is thus assumed to be broken.

According to another aspect, the method permits determining quality for different sections of an ingot, where each section corresponds to one wafer. In this embodiment, the method comprises: assigning inspection data to each cell, assigning a wafer position (in the ingot) to each wafer, and upon match between a cell image and a wafer image, assigning cell inspection data to each wafer position in the ingot. These cell inspection data may include breakage of wafer during production process.

Assigning wafer position to each wafer and also inspection data to each cell are current procedures in the field of solar cell production and will thus not be discussed in detail.

Ingot quality data for each section (wafer) which are derived from this process, will permit analysis of the ingot's production process. A feedback system can then be implemented for adjusting process variables to obtain even good quality in the ingot. According to this, one aspect of the invention comprises adjusting ingot and/or wafer production parameters based on cell inspection data.

The method according to the invention requires provision of cell and wafer images. These images can be provided by means of at least one CCD camera, a CMOS camera, a digital camera, an IR depicting system or any other depicting system. The suitable system has to have a sufficient definition/resolution to provide an almost unique crystallographic image for each wafer/cell.

There may be several imaging devices arranged in different locations in the production process. This will provide more detailed information of the quality of the manufacturing steps, and thus enable more precise adjustments of the process variables.

According to another aspect, the method permits determining quality (electrical and mechanical) for different production equipment in the wafer and cell production processes. In this embodiment, the method comprises: assigning inspection data to each cell, assigning substantially complete manufacturing history to each wafer, and upon match between a cell image and a wafer image, including cell inspection data in each wafer manufacturing history.

Image data will be achieved by means of "fingerprint matching" software, that is image recognition software available in the market.

It is possible to implement one embodiment of the method where correspondence is established by means of image matching together with other methods, for example data tracking of the wafers. In this case, as the methods will complement one another, it will be possible to achieve satisfactory results without requiring high definition in the imaging system nor a complete data tracking.

By means of the invention it is also possible to create a database comprising cell/wafer images which are stored independently or linked to one another. Such a database will be highly useful for e.g. computing statistics. According to this, in one aspect, the method comprises storing the wafer image and the cell image in a memory before and/or after assigning the current cell to the current wafer.

The invention comprises also a method for controlling production parameters in a solar cell and/or wafer production process, comprising, apart from the above mentioned:
 providing the ingot position data and/or manufacturing history for each wafer,
 providing inspection data for the cell,
 upon match between a cell image and a wafer image, assigning the current cell's inspection data to the current wafer position in the ingot and/or the manufacturing history of the wafer.

This method provides ingot data related to each wafer position in the ingot.

In one aspect, the latter method comprises regulating ingot and/or wafer production based on cell inspection data assigned to wafer manufacturing history and identity, e.g. wafer position in ingot and other elements of the wafer manufacturing history. Of course it will be possible to use these parameters also for controlling cell production.

The cell inspection data may include wafer breakage as noted above.

The invention comprises also a system for establishing correspondence between wafers and solar cells produced from said wafers, comprising:
 at least one imaging device for providing images of the wafers and the cells,
 a processing unit for comparing a wafer image to a cell image, and upon match between a cell image and a wafer image, assigning the current cell to the current wafer, and
 a memory unit.

In one aspect of the invention the imaging device is adapted to provide images of the crystallographic structure of the wafer and the cell and the processing unit is adapted to compare the crystallographic structure of the wafer and the cell to one another.

The term "imaging device" refers here to all equipment which is necessary to provide an image depicting the crystallographic structure, that is not only devices adapted to provide an image but also hardware devices adapted to process said image in order to provide crystallographic information regarding the wafer and the cell.

In one aspect of the invention the processing unit is adapted to assign wafer identification data to the corresponding cell. Wafer identification data can be inputted to the processing unit by known means, e.g. a personal computer or another user interface devices.

In another aspect the processing unit is connected to a cell inspection unit providing cell inspection data, and is adapted to
 assign inspection data to each cell,
 assign a wafer position to each wafer, and
 upon match between a cell image and a wafer image, assign cell inspection data to each wafer position.

If breakage of a wafer occurs during cell manufacturing, that particular wafer will be removed from the production line and there will not be a cell image matching the wafer image of that wafer. If no cell image match a particular wafer image, this wafer is assumed to be broken.

It is also possible for the processing unit to receive cell inspection data via a manual input device (operator input) or other types of input devices (data file).

In a further aspect of the invention, the processing unit is connected to devices for ingot and/or wafer production control. In a further aspect, it is adapted to adjust ingot and/or wafer production parameters based on cell inspection data.

The cell inspection data may include wafer breakage as noted above.

In a further aspect of the invention, the system comprises two imaging devices.

Said imaging device(s) can be alike or different, and can be implemented, both in the case where a single device is used and where two devices are used by means of a CCD camera, a digital camera or an IR depicting system. One image device can be used for depicting the wafer while the other can be used for depicting the cell.

There may be even more imaging devices arranged in different locations in the production process to provide more detailed information of the different manufacturing steps. This will enable more precise adjustments of the process variables.

In one embodiment of the invention, the memory unit is adapted to store the wafer image and the cell image in a memory before and/or after a cell is assigned to a wafer.

The invention comprises also a system as mentioned above and adapted for controlling production parameters in a solar cell production process, comprising:
 a unit for providing wafer position data and/or manufacturing history,
 a cell inspection unit for providing inspection data for each cell,
 where the processing unit in the system is adapted for, upon a match between a cell image and a wafer image, assigning the current cell's inspection data to the current wafer and/or wafer position.

According to one aspect of this system, the processing unit is adapted to regulate ingot and/or wafer production based on cell inspection data assigned to wafers and/or wafer positions.

BRIEF DESCRIPTION OF THE DRAWINGS

The invention will now be described by means of an example illustrated in the drawings, where.

DETAILED DESCRIPTION OF THE INVENTION

Figure 1:
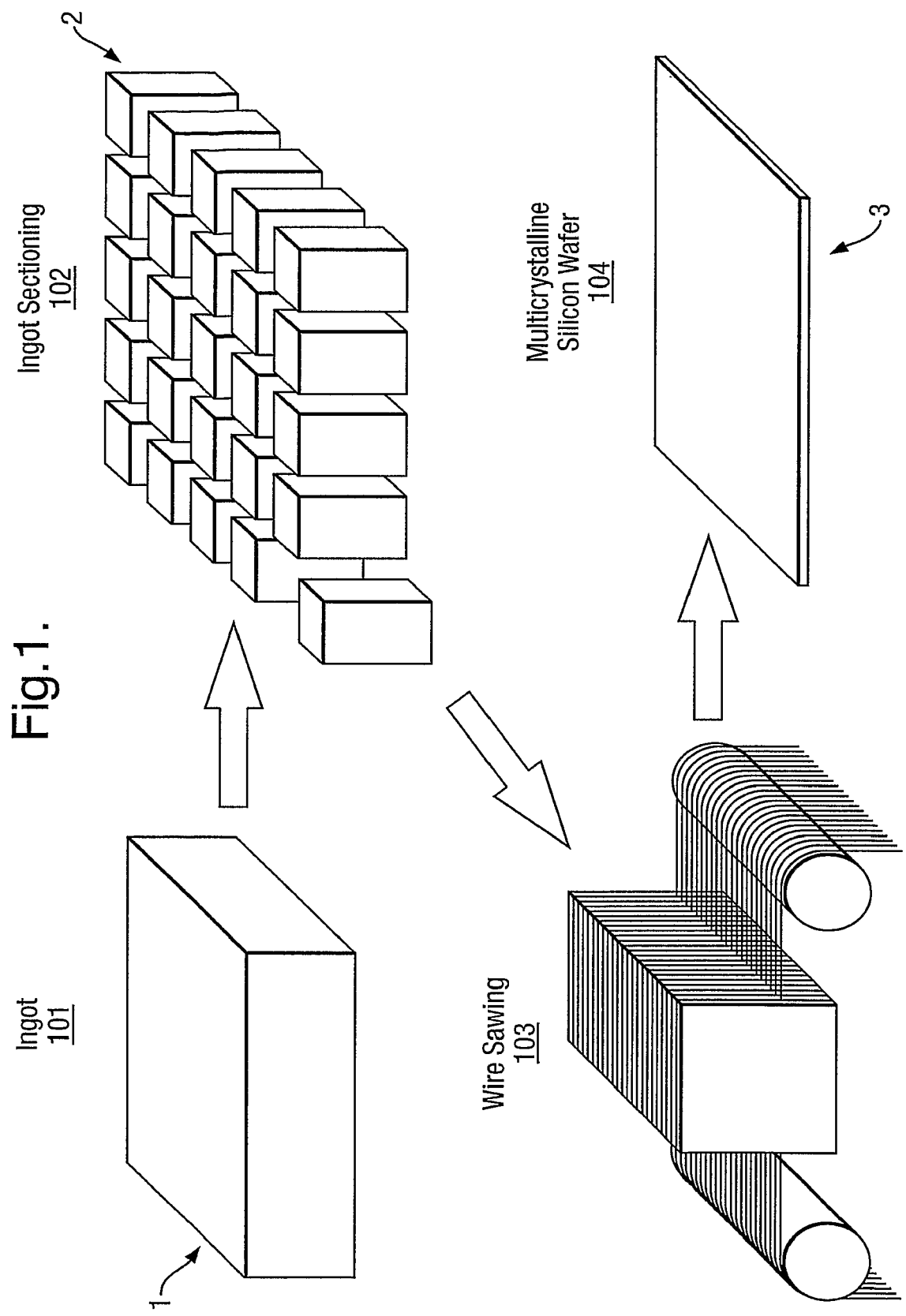
FIG. 1 is a block diagram illustrating an example of wafer manufacture.

FIG. 1 is a block diagram illustrating wafer manufacture. The point of departure (step 101) is a silicon ingot 1. This ingot is first sectioned into smaller ingots 2 (step 102), and these are sawed (step 103) by means of wire saws into wafers 3 (step 104). As one can see, the grain structure of the wafer is not modified during this production process.

Figure 2:
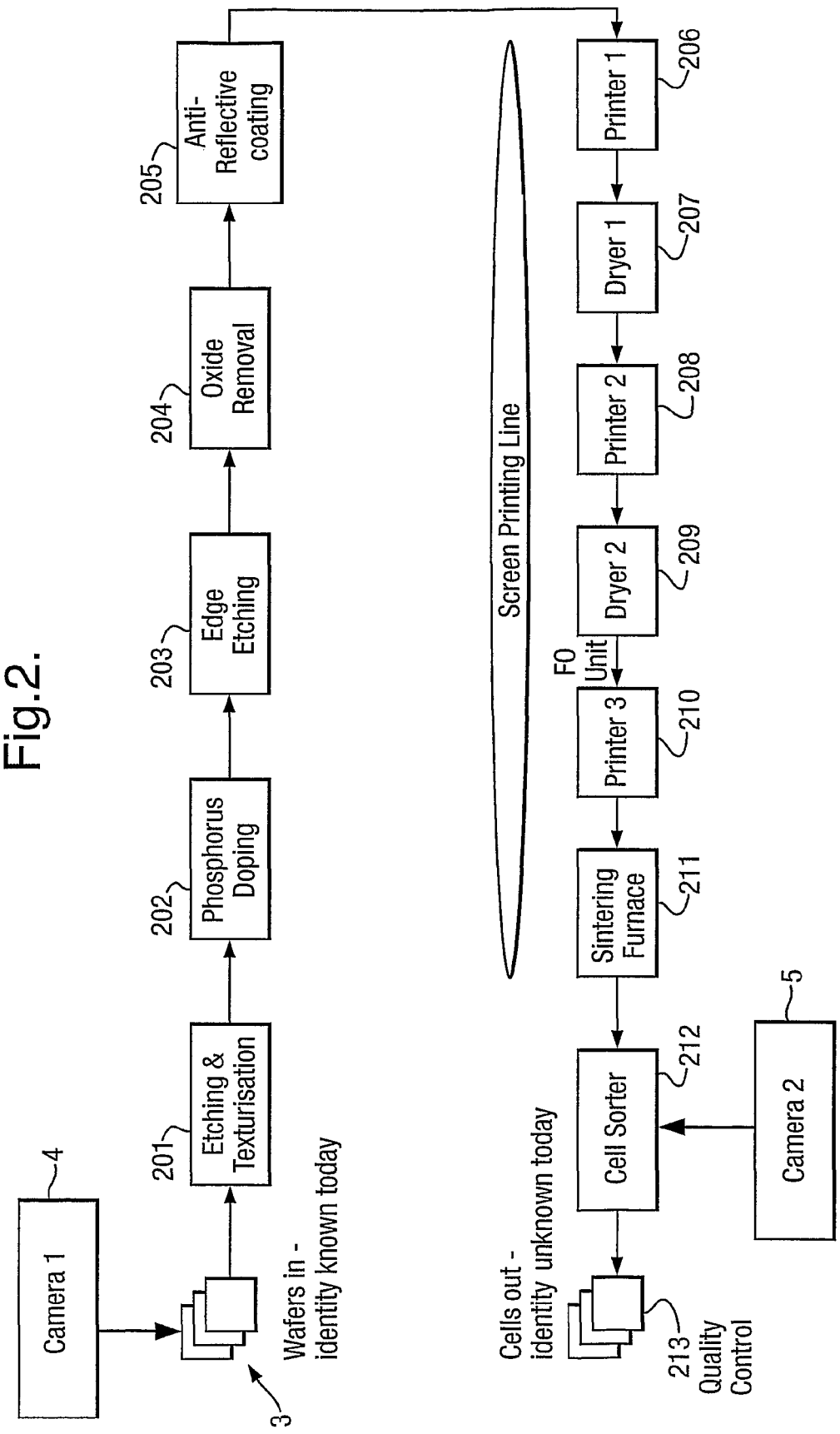
FIG. 2 is a block diagram illustrating an example of cell manufacturing.

FIG. 2 shows the cell manufacturing process, and imaging devices 4 and 5 for providing images of the wafer and the cells. The process starts with wafers 3 which were cut out from ingot 1 in FIG. 1. In step 201, the wafers are subject to etching and texturisation, in step 202 a phosphorus doping is performed, in step 203 the edges of the wafers are etched, in step 204 the oxide layer on the wafer is removed. In step 205 an anti reflective coating is applied on the surface. After these steps, the wafer enters a screen printing line. In this screen printing line, the wafer is processed by means of a first printer (step 206), a first dryer (step 207), a second printer (step 208) and a second dryer (step 209). After this follows a third printer (step 210) and a sintering process in a furnace (step 211) followed by a cell sorting procedure (step 212). When the cells are finished, a quality control is performed (step 213).

As shown in the figure, a first imaging device 4, in this case a camera, is adapted to provide an image of each wafer before the cell manufacturing process starts. During the sorting step, an image of each cell is provided by means of a second imaging device 5.

Figure 3:
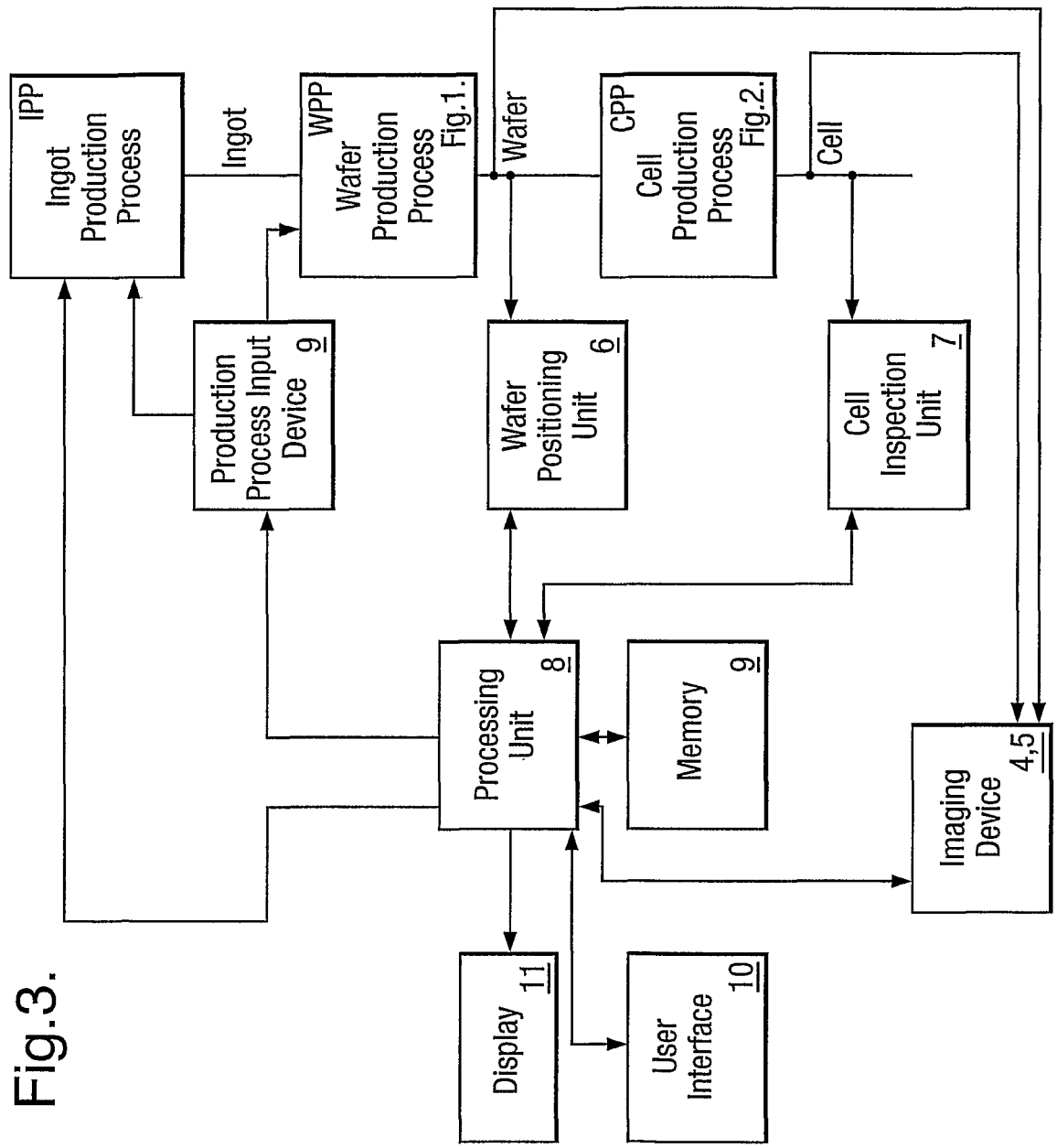
FIG. 3 is a block diagram illustrating one embodiment of the invention.

FIG. 3 shows an embodiment of the system according to the invention. Said system comprises:
- one or several imaging devices 4, 5 for providing wafer and cell images,
- a unit 6 for providing wafer position data, the function of this unit being to provide data regarding original position of each wafer in an ingot,
- a cell inspection unit 7 for providing inspection data for each cell, this cell inspection unit performs the quality control operation in step 213 in FIG. 2,
- a processing unit for comparing each wafer image to a cell image to identify the original wafer for each cell and for assigning cell inspection data to the corresponding wafer and/or wafer position,
- a memory unit (9) for storage of processing instructions and data.

In one embodiment of the system, the processing unit is adapted to regulate ingot and/or wafer production (IPP, WPP) based on cell inspection data assigned to wafers and/or wafer positions. This is shown in FIG. 3, where processing unit 8 can control the ingot production process directly, or via a production process input device 9 can send commands to processing unit(s) which control the ingot and wafer production process. Although it is not shown in the figure, it is also possible to control cell production process (CPP) by means of processing unit 8.

The system can also comprise a user interface 10 for input of commands and data regarding ingot/wafer/cell, and a display for communication with a user.

FIG. 3 shows also in which steps of the process data regarding ingot/wafer/cell are collected, where this data comprises wafer and cell image, wafer position information, cell inspection data, etc.

As one can see, the invention provides reliable and swift feedback regarding process quality and permits thus adjustment of process parameters to achieve a better result.

Figure 4:
FIG. 4 is an example of a wafer image.
Figure 5:
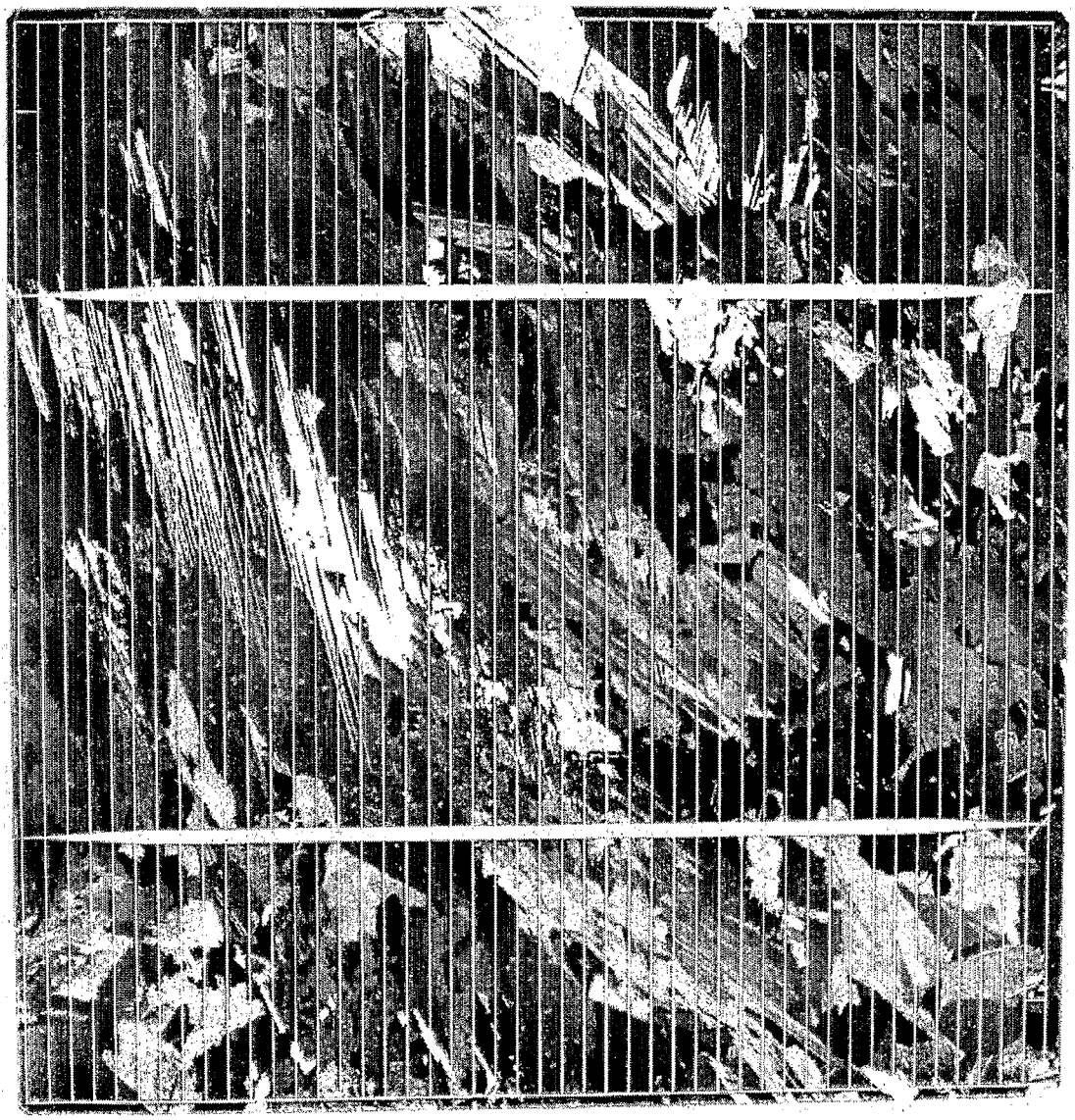
FIG. 5 is an example of a cell image.

FIG. 4 shows an image of a wafer before start of the manufacturing process, and FIG. 5 shows an image of a cell resulting from the manufacturing process. As one can see, the crystallographic structure can clearly be recognized in the images, and this structure will be unique for each wafer and the corresponding cell.

The invention claimed is:

1. System for producing solar cells, comprising:
   sectioning devices for manufacturing wafers from a silicon ingot,
   wafer processing devices for producing a solar cell;
   at least one imaging device for providing images of wafers and cells;
   a processing unit for comparing a wafer image to a cell image, and upon match between a cell image and a wafer image, assigning the current cell to the current wafer; and
   a memory unit.

2. System according to claim 1, characterized in that the imaging device is adapted to provide images of the crystallographic structure of the wafer and the cell and the processing unit is adapted to compare the crystallographic structure of the wafer and the cell to one another.

3. System according to claim 1 or 2, where the processing unit is adapted to assign wafer identification data to the corresponding cell.

4. System according to claim 3, where the processing unit is connected to a cell inspection unit providing cell inspection data, and is adapted to:
   assign inspection data to each cell;
   assign a wafer position to each wafer; and
   upon match between a cell image and a wafer image, assign cell inspection data to each wafer position.

5. System according to claim 4, wherein the processing unit comprises instructions arranged to assign "breakage" as inspection data for the wafer position when no match between the wafer image and the cell image is found at that wafer position.

6. System according to claim 4, where the processing unit is connected to an input device for ingot and/or wafer production control, and/or is adapted to
   adjust ingot and/or wafer production parameters based on cell inspection data.

7. System according to any of the preceding claims, comprising two imaging devices.

8. System according to any of the preceding claims, wherein the imaging device(s) is a CCD camera, a digital camera or an IR depicting system.

9. System according to any of the preceding claims, where the memory unit is adapted to store the wafer image and the cell image in a memory before and/or after a cell is assigned to a wafer.

10. System according to any of the preceding claims and adapted for controlling production parameters in a solar cell production process, characterized in that it comprises:
    a unit for providing wafer position data and/or manufacturing history;
    a cell inspection unit for providing inspection data for each cell;

and that the processing unit is adapted to upon a match between a cell image and a wafer image, assigning the current cell's inspection data to the current wafer and/or wafer position.

11. System according to claim 10, where the processing unit is adapted to regulate ingot and/or wafer production based on cell inspection data assigned to wafers and/or wafer positions.

12. Method for establishing correlation between wafers and solar cells produced from said wafers, comprising,
   a) providing a silicon wafer having a unique crystalline structure;
   b) capturing an image of the wafer with an imaging device, said imaging device being arranged to render images of sufficient resolution to enable identification of the wafer's crystalline structure;
   c) providing a solar cell manufactured from a silicon wafer, said solar cell having a unique crystalline structure corresponding to the crystalline structure of the wafer from which it was manufactured;
   d) capturing an image of the solar cell with an imaging device, said imaging device being arranged to render images of sufficient resolution to enable identification of the solar cells's crystalline structure;
   e) comparing the image of the wafer to the image of the solar cell in a processing unit, said processing unit comprising image-recognition software adapted for the recognition and comparison of crystalline structures; and
   f) establishing, based upon the results of the comparison of images by the processing unit, a correlation or lack thereof between the wafer and the solar cell.

13. A method according to claim 12, wherein the imaging device is a CCD camera, a CMOS camera, a digital camera or an IR depicting system.

14. A Method according to claim 13, further comprising storing the images of the wafer and the solar cell in the memory of a computer.

15. A method according to claim 14, further comprising the steps of
   gathering inspection data for the solar cell, and entering this data in the memory of the computer;
   gathering manufacturing history data for the wafer, and entering this data in the memory of the computer;
   in the event of a positive correlation between the solar cell and the wafer, including the solar cell inspection data in the manufacturing history of the wafer; and
   storing the data in a data base, stored in the memory of the computer.

16. A method according to claim 15, wherein the manufacturing history data for the wafer comprises position data related to the wafer's position in a ingot from which it was manufactured.

17. A method for the production of solar cells, comprising
   a) providing a silicon ingot;
   b) sectioning the ingot;
   c) cutting silicon wafers from the ingot, each of said wafers having a unique crystalline structure;
   d) gathering and storing manufacturing history data of the wafers in the memory of a computer;
   e) capturing an image of the wafer with an imaging device, said imaging device being arranged to render images of sufficient resolution to enable identification of the wafer's crystalline structure;
   f) storing the image of the wafer in the memory of a computer;
   g) processing, by the use of specially adapted processing apparatus, the wafers into solar cells, each said solar cells having a unique crystalline structure corresponding to the crystalline structure of the wafer from which it was manufactured;
   h) gathering and storing inspection data for the solar cells in the memory of the computer;
   i) capturing an image of the solar cell with an imaging device, said imaging device being arranged to render images of sufficient resolution to enable identification of the solar cells's crystalline structure;
   j) storing the image of the solar cell in the memory of the computer, said computer being loaded with image-recognition software adapted for the recognition and comparison of crystalline structures;
   k) comparing the images of the wafers with image of the solar cells in the computer, and establishing, based upon crystalline structure comparison, the identity of the wafer from which a particular solar cell was created; and
   l) based upon the inspection data of the solar cell, adjusting manufacturing parameters for the wafers.

18. A method according to claim 17, wherein the manufacturing parameters of the wafer comprise the position in the ingot from which it was cut.

19. A method according to claim 17, wherein the inspection data for the solar cells comprises breakage data.

* * * * *